United States Patent
Widlund

[11] Patent Number: 5,961,507
[45] Date of Patent: Oct. 5, 1999

[54] ABSORBENT BODY WHICH INCLUDES CAVITIES

[75] Inventor: Urban Widlund, Mölnlycke, Sweden

[73] Assignee: SCA Hygiene Products AB, Goteborgs, Sweden

[21] Appl. No.: 08/849,692
[22] PCT Filed: Dec. 28, 1995
[86] PCT No.: PCT/SE95/01592
§ 371 Date: Jan. 11, 1997
§ 102(e) Date: Jan. 11, 1997
[87] PCT Pub. No.: WO96/20671
PCT Pub. Date: Jul. 11, 1996

[30] Foreign Application Priority Data

Dec. 30, 1994 [SE] Sweden .................................. 9404583

[51] Int. Cl.⁶ ....................................................... A61F 13/15
[52] U.S. Cl. ........................................ 604/378; 604/385.1
[58] Field of Search ..................................... 604/358, 378, 604/385.1

[56] References Cited

U.S. PATENT DOCUMENTS

| | | |
|---|---|---|
| 3,889,679 | 6/1975 | Taylor . |
| 5,110,386 | 5/1992 | Ochi et al. ............................. 604/385.1 |
| 5,454,800 | 10/1995 | Hirt et al. ................................. 604/358 |
| 5,669,895 | 9/1997 | Murakami et al. ....................... 604/378 |

FOREIGN PATENT DOCUMENTS

| | | |
|---|---|---|
| 0 393 953 A2 | 10/1990 | European Pat. Off. . |
| 0539032A1 | 4/1993 | European Pat. Off. ............... 604/378 |
| 2 266 444 | 11/1993 | United Kingdom . |
| 2 286 126 | 8/1995 | United Kingdom . |
| WO 94/10956 | 5/1994 | WIPO . |
| WO 95/07673 | 3/1995 | WIPO . |

Primary Examiner—John G. Weiss
Assistant Examiner—Dennis Ruhl
Attorney, Agent, or Firm—Burns, Doane, Swecker & Mathis, L.L.P.

[57] ABSTRACT

An absorbent article which includes a liquid-permeable outer sheet (1) mounted on a first surface of the article, a liquid-impermeable outer sheet (2) mounted on a second surface of the article, and an absorbent body (3) which is enclosed between the two casing sheets and which includes a receiving space (24) for receiving and accommodating body liquid or fluid, the space comprising at least one cavity or region of lower density than the density of a part of the absorbent body (3) located adjacent the receiving space (24) generally in the same plane. The article is characterized in that the receiving space (24) is disposed in a storage layer (19) in the absorbent body (3), wherein the storage layer (19) is formed from a web of material which is divided in the longitudinal direction of the web along a dividing curve (20) which is undulating along at least part of its length so as to cross a line (21) extending in the longitudinal direction of the web at least two times, and the web-parts (22, 23) are displaced relative to one another in the plane of the web such that the web-parts (22, 23) will define the receiving space (24) therebetween in the plane of the web.

21 Claims, 4 Drawing Sheets

ABSORBENT BODY WHICH INCLUDES CAVITIES

The present invention relates to an absorbent article which includes a liquid-permeable outer sheet disposed on a first article surface, a liquid-impermeable outer sheet disposed on a second article surface, and an absorbent body which is enclosed between the two outer sheets and which includes a receiving space in which body liquid is taken up, said space consisting in at least one cavity in the absorbent body.

Hitherto, the problem encountered with absorbent articles, such as diapers, incontinence guards, sanitary napkins or like articles which are intended to repeatedly receive and absorb body liquid, or fluid, discharged by a user is that the rate at which the liquid is able to penetrate into the article decreases considerably with each new wetting occasion. This problem is particularly pronounced in diapers and incontinence guards that are intended for children and adults, since in these cases the quantities of liquid that the article will receive and absorb are relatively large and are discharged within the space of only a few seconds. It is therefore not unusual, particularly after a first wetting of the article, that the liquid which is not able to penetrate into the article immediately will instead flow over the surface of the article and leak past the edges thereof. Such leakage of body liquid is naturally highly undesirable, since it is liable to soil the clothes, bed linens and mattresses used by the wearer, and even stain and destroy such commodities.

The reason why the body liquid penetration rate decreases with repeated wetting of the article is because the absorbent body of the article becomes saturated with body liquid temporarily within a limited area around the area on the article surface in which the body liquid first impinges, the so-called primary wetting area. The absorbent articles are normally comprised of one or more layers of hydrophilic fibres, for instance cellulose fluff pulp, and often also include a powerful absorbing hydrocolloidal material, so-called superabsorbents. Liquid is transported relatively slowly through such materials, since transportation of the liquid is mainly governed by the capillary forces acting in the cavities located between fibres and particles in the absorbent body of the article. Liquid is transported within the hydrocolloidal materials by diffusion, which is a still slower process than the process generated by the capillary forces. The liquid will therefore remain in the primary wetting area of the article for a relatively long period of time and will then gradually be transported out to surrounding parts of the absorbent body.

It is known to provide the article with liquid-transporting means in the form of compressed patterns, for instance compressed stripes, which function to disperse the liquid in the longitudinal direction of the article, so as to steer the transportation of liquid away from the primary wetting area to parts of the absorbent body in which absorbent material is still unused. An article possessing such compressed stripes is earlier known from PCT/SE94/00835. Liquid transportation in the article is mainly the result of the differences in capillary forces acting between the compressed stripes and surrounding material. Even though a positive effect is obtained in this case in the form of a directed liquid flow in the absorbent body, the rate at which liquid is transported in the article is much too slow in relation to the rate at which body liquid is discharged to the article. Consequently, there is a risk that liquid will not be absorbed quickly enough, but instead will run along the surface of the article and out over the edges thereof, resulting in leakage, this risk being particularly manifest in products which are intended for urine absorption, such as diapers and incontinence guards, onto which large quantities of liquid are often discharged over a short period of time. Furthermore, heavy compression of the article results in rigid parts which do not flex easily and which prevent the article from following satisfactorily the movements of the wearer's body and conforming to the shape of the wearer's body in use.

Another method of obtaining an effective and instant ability to receive and retain large volumes of body liquid is to create different types of liquid-receiving cavities, or basins, in the article.

U.S. Pat. No. 3,889,679 describes a diaper in which a plurality of circular holes extend through the absorbent body of the diaper. These holes are intended to receive and accommodate liquid discharged to the diaper over a short period of time. The absorbent material surrounding the holes then absorbs the liquid by suction. Such liquid receiving holes fulfil their function relatively well, at least upon initial wetting of the diaper. The manufacture of a cavitated absorbent body, however, is a relatively complicated procedure.

Swedish Patent Application No. 9304321-4 describes an absorbent body for absorbent articles such as diapers, incontinence guards and sanitary napkins, which is provided with a liquid-receiving part in the form of a well which is located generally opposite the anticipated primary wetting area of the absorbent body and which extends depth-wise into and through a liquid storage part in the absorbent body. The well is in liquid communication with a liquid-dispersion layer disposed beneath a liquid storage layer and has a larger effective mean pore size than the surrounding liquid storage part.

An absorbent body of this kind also fulfils the function of receiving and accommodating a large quantity of body liquid, or fluid, discharged abruptly to the diaper. The manufacturing process of the absorbent body, however, is complicated, particularly in the case of high production rates.

The object of the present invention is therefore to provide a simple and inexpensive method of producing liquid-receiving cavities, channels or like configurations in an absorbent layer or sheet, essentially without wasting material.

This object is achieved in accordance with the invention with the aid of a method which is characterized by forming the receiving space in a storage layer in the absorbent body, wherein the storage layer is formed from a web of material which is divided in the longitudinal direction of the web along a dividing curve which undulates along at least a part of its length such as to cross at least twice a line extending in the longitudinal direction of the web; and by displacing the web-parts in relation to one another in the plane of the web such that the web-parts will define the receiving space therebetween in the plane of the web.

According to one embodiment of the invention, the web-parts are displaced relative to one another in the longitudinal direction of the dividing or separating curve, such that the web-parts will define at least one cavity therebetween.

According to another embodiment, the web-parts are displaced in a direction away from one another in the transverse direction of the web, whereby the storage layer exhibits a channel-like undulating space extending between the web-parts.

The web-parts may be placed in the article with the undulating curve extending either in the longitudinal or in the transverse direction of the article.

By undulating curve is meant any desired curve form, such as a sinusoidal curve, sawtooth curve, square-wave curve, etc. The waves or undulations may extend along a straight, curved or wavy line.

According to a further embodiment of the invention, the web-parts are displaced mutually in the longitudinal direction of the web such that the dividing curve maxima on respective sides of the line extending longitudinally in the web will be located essentially opposite one another, and such that a line extending generally perpendicular to the line extending longitudinally through the web can be drawn through the maxima of said dividing curve, whereby the web-parts define therebetween a row of holes alternating with intermediate overlapping web-parts in the longitudinal direction of the web.

The size of the holes can be varied by varying the amplitude of the waves or undulations, for instance so that the holes in the wetting area will be larger than the holes outside the wetting area.

In the case of a particularly preferred embodiment, those parts of the storage layer that lie adjacent the storage space include a material which increases in volume in a direction generally perpendicular to the first surface of the article when wetted, whereby the size of the storage space also increases in said direction as a result of wetting of the article.

A suitable material in this regard is formed from a particle material which includes flash-dried cellulose fibres that have been dry-formed to provide a web having a surface weight of 30–2000 g/m$^2$ and compressed to a density of between 0.2–1.2 g/cm$^3$, said web being incorporated in the article without subsequent defibration and fluff formation.

Another suitable material is formed from an air-laid web of cellulose fibres which is compressed to a dry-form sheet having a first density of between 0.2–1.2 g/cm$^3$, whereafter the sheet is softened mechanically to a second density which is lower than the original density and therewith delaminated so as to form a plurality of incompletely separated thin fibre layers whose density corresponds to the first density.

Other examples of suitable storage layer materials are an air-laid web of cellulose fluff pulp which has been compressed to a density of at least 0.1 g/cm$^3$ preferably at least 0.12 g/cm$^3$, and an air-laid web of cellulose fluff pulp having mixed therein a given proportion of thermoplastic fibres, whereafter the fibre web has been thermobonded. The air-laid web of cellulose fluff pulp may also include a given proportion of superabsorbent. Wet-laid fibre structures may also be used in accordance with the invention.

Another suitable storage layer is formed from a web of material having a first thickness and including resilient material, wherein the web is compressed at right angles to a plane through the web to a second thickness and is bonded in its compressed state with the aid of a binder that will dissolve in body liquid, wherein bonding of the web ceases when the web is wetted and the storage layer returns at least partially to the first thickness.

Alternatively, the storage layer may be comprised of a compressed foam material which will expand in its thickness direction when wetted, or of a compressed fibre layer which comprises at least partially fibres which have a given resiliency in a wet state.

The receiving space in the storage layer may either comprise one or more holes which extend through the thickness of the storage layer or at least one channel-like cavity which extends in the longitudinal direction of the article.

According to one embodiment, the proportion of storage layer volume that is comprised of the receiving space is largest within the primary wetting area of the article, i.e. that area of the article which is intended to be first wetted by body liquid. The proportion of the storage layer taken-up by the receiving space decreases, suitably in a direction away from the primary wetting area.

Holes and channel-like cavities can be formed readily in a layer of material without incurring wastage, by dividing the web along an undulating curve and then displacing the thus separated web-parts in relation to one another. When the web-parts are displaced so as to form a row of openings which alternate with parts where the web-parts overlap one another, the overlapping parts of material can provide further advantages. For instance, this enables the absorption capacity of an absorbent article which includes an absorbent layer formed from such a web of material to be increased, since the overlapping parts therewith have twice the absorption capacity of the remainder of the absorbent layer. The absorbent layer is advantageously arranged so that the overlapping parts will be located where a higher absorption capacity is most desirable. In the case of a diaper, sanitary napkin or like article, it may be suitable for the overlapping parts to be located in the crotch part of the article, i.e. the part of the article which lies in the crotch region of the wearer in use. The crotch part is that part of the article in which essentially all liquid is absorbed primarily.

However, it is suitable to provide within that region of the crotch part which is expected to be wetted by discharged body liquid first, i.e. the primary wetting area, liquid-receiving cavities in which the liquid can be accommodated prior to being absorbed by the surrounding absorbent material.

Another advantage afforded by the overlapping parts is that when these parts are formed from a material which expands in the thickness direction when wetted, said parts will function as spacing means between the wet absorbent body and the wearer.

The method applied in dividing the web is not significant to the invention. Any conventional cutting or clipping method can be used. For instance, the web can be divided by cutting the web apart with the aid of a knife roll, by cutting with the aid of ultrasonic cutters, high pressure water jets, lasers, or like devices.

A number of different cutting curves and variants in displacing different web-parts in relation to one another are conceivable within the scope of the invention. For instance, the undulating cutting curves need not have the same amplitude along the whole of their lengths, and the curve may have two or several maximal amplitudes. All types of cutting curves which cross a line extending longitudinally in the web at an appropriate frequency can be used, provided that they will result in at least two web-parts which extend in the longitudinal direction of the web and which can be displaced mutually such as to define together an intermediate cavity.

BRIEF DESCRIPTION OF THE DRAWINGS

The invention will now be described in more detail with reference to the accompanying drawings.

DESCRIPTION OF EMBODIMENTS

Figure 1:
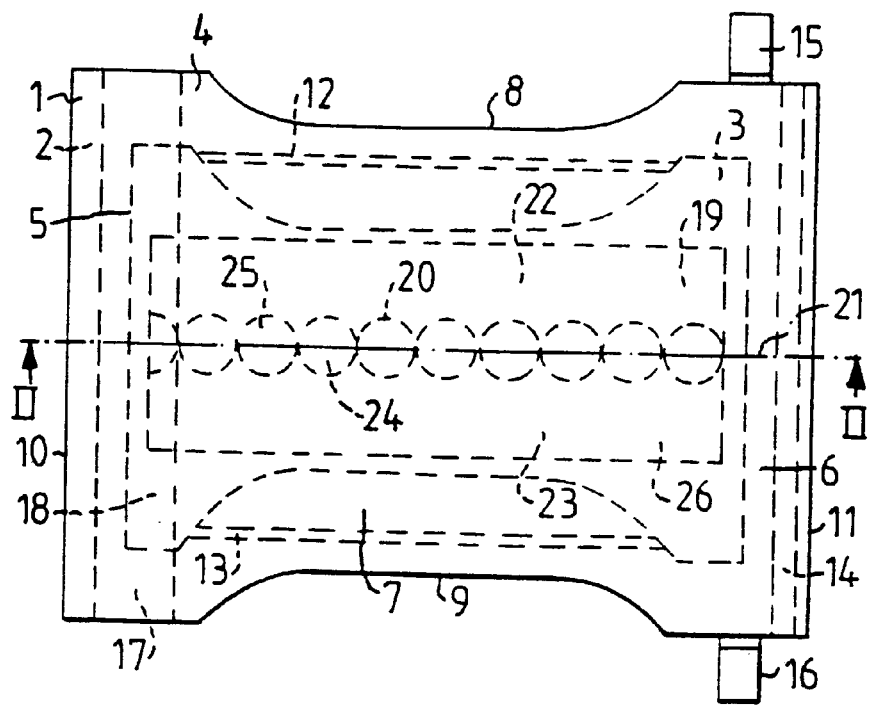
FIG. 1 illustrates from above a diaper constructed in accordance with a first embodiment of the invention.
Figure 2A:
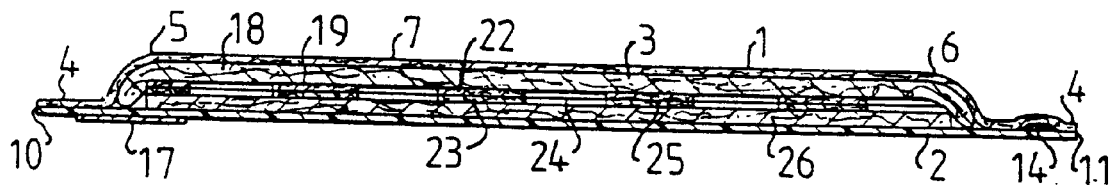
FIG. 2a is a longitudinal sectioned view of the diaper shown in FIG. 1, taken on the line II—II prior to wetting the diaper.
Figure 2B:
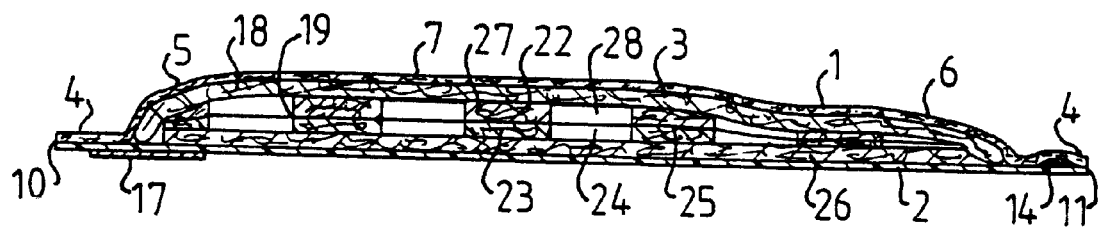
FIG. 2b is a longitudinal sectioned view of the diaper shown in FIG. 1, taken on the line II—II after wetting the diaper.

The diaper illustrated in FIGS. 1, 2a and 2b is seen from the side which lies proximal to the wearer in use. The diaper is shown extended in a flat state and includes a liquid-permeable first casing sheet 1, made for instance of non-woven material, woven material, perforated plastic film or net mounted on that side of the diaper which is intended to lie proximal to the wearer in use. A liquid-impermeable second casing sheet 2 made, for instance, of plastic film or a nonwoven material or woven material that has been made hydrophobic, is mounted on that side of the diaper which is intended to lie distal from the wearer in use. The two casing sheets 1, 2 embrace an absorbent body 3 and are mutually joined together within parts 4 of the casing sheets 1, 2 that project out around the absorbent body 3.

The diaper is constructed so that it will embrace the lower part of the wearer's torso in a pants-like fashion when in use. To this end, the diaper has a front part 5 which, in use, is intended to face forwardly of the wearer and lie over the wearer's stomach, a rear part 6 which, in use, is intended to face rearwardly of the wearer and lie in abutment with the wearer's buttocks, and a crotch part 7 disposed between the front part 5 and the rear part 6 of the diaper and intended, in use, to be located in the crotch area between the wearer's thighs. The diaper has a generally hourglass shape, wherein its front part 5 and rear part 6 are broader than the crotch part 7. The diaper also includes two longitudinally extending side-edges 8, 9 and a front waist edge 10 and a rear waist edge 11. When the diaper is worn, the longitudinally extending side-edges 8, 9 form the edges or borders of the leg openings of the diaper, whereas the waist edges 10, 11 together embrace the waist of the user and form the waist edge or border of the diaper.

An elastic device 12, 13 is mounted along each respective side-edges 8, 9 of the diaper. The elastic devices 12, 13 are mounted on the diaper in a stretched state and when contracting gather in the side-edges 8, 9 of the diaper and curve the diaper into a trough-like shape. The effect of the elastic devices 12, 13 is not apparent from FIG. 1, however, since the diaper is shown in a flat state with the elastic devices 12, 13 in a stretched state. In use, the elastic devices 12, 13 function to hold the edges of the diaper leg openings in sealing abutment with the wearer's thighs. A further elastic device 14 is mounted along the rear waist edge 11 of the diaper, so as to obtain sealing abutment with the edge of the waist opening in a corresponding manner. Several different types of elastic devices 12–14 suitable for this purpose are known to the art, such as elastic threads, elastic bands, elastic nonwoven, or like materials.

In order to enable the diaper to be secured in use in a pants-like form around the wearer's body, a fastener tab 15, 16 is provided on a respective side-edge 8, 9 in the proximity of the rear waist edge 11. The fastener tabs 15, 16 are intended to coact with and fasten against a fastener receiving region 17 provided on the front diaper part 5. The fastener tabs 15, 16 are normally in the form of self-adhesive tapes which prior to use are folded over with the adhesive-coated surface lying against and protected by a fastener tab area that has been treated with a release agent, or on the diaper itself. The receiving region 17 is comprised of a reinforced region of the liquid-impermeable casing sheet 2 on the front part 5 of the diaper. This reinforcement is simplest achieved by laminating a plastic film strip on that side of the liquid-impermeable casing sheet 2 that lies distal from the absorbent body 3. This reinforcement of the receiving region 17 enables the diaper to be opened and refastened without tearing the liquid-impermeable casing sheet 2.

Alternatively, the fastener tabs 15, 16 may comprise any appropriate type of mechanical fastener means, such as one part of a Velcro® tape fastener, a press stud or equivalent means. In this regard, the receiving region 17 will be comprised of the corresponding part of the mechanical fastener device. It is also known to use fastener means which can be considered essentially as hybrids between adhesive fastener devices and mechanical fasteners. An example in this regard is described in EP-A-393,953. No fastener devices are required in the case of diapers which are intended to be supported as inserts in a pair of tightly fitting pants. So-called pants-type diapers, or trainers, also normally lack fastener devices.

The absorbent body 3 includes a first absorption layer, the liquid or fluid-receiving layer 18, which has essentially the same shape and size as the diaper itself and which is located nearest inwardly of the liquid-permeable casing sheet 1. The liquid-receiving layer 18 is suitably comprised of a soft material of high liquid-permeability and having relatively large pores or capillaries. An example of such material is lightly compressed cellulose fluff layers, in particularly comprised of mechanical, thermomechanical or chemithermomechanical (CTMP) pulp, or fibre mats and wadding of other kinds comprised of natural fibres or of synthetic fibres. Mixtures of cellulose fluff pulp, or other cellulose based fibres, with different types of synthetic fibres may also be used. It is also possible to use soft perforated or open-cell foam material. Such material has a low liquid dispersion capacity, whereby the wet area of the layer will remain restricted essentially to the primary wetting region even after repeated wetting of the layer or sheet. The wearer thus feels the surface of the diaper in contact with the wearer to be dry and comfortable against the skin, even after having worn the diaper for a relatively long time.

When the diaper is in use, the receiving layer 18 is intended to receive discharged body liquid and to transport the liquid away from the liquid-permeable casing sheet 1 and will therefore have large pores which offer as little resistance as possible to the liquid flow. The receiving layer 18 will preferably also be soft and feel comfortable against the wearer's skin during the full period of its use. The properties of the material in the receiving layer 18 will preferably not therefore change essentially after being wetted. It is also desirable for the material to have a given resiliency, so that it will endeavour to return to its original state after being compressed or wrinkled, pleated, in use.

When the receiving layer 18 includes cellulose fibres which normally have a relatively low resiliency in a wet state, for instance chemical pulp, it may be suitable to admix the cellulose fibres with another material which will enhance the wet resilience of the material and therewith impart to the first absorption layer a given degree of resilience even in a wet state. Examples of such materials include different types of thermoplastic fibres or particles which, when the layer is heated, will function to bind the fibres in the layer and therewith fixate the fibres in their mutual positions and therewith impart to the layer a higher tensile strength and improved resiliency in both a wet and a dry state. Cellulose fibres can also be modified chemically, e.g. by cross-linking, such as to enhance their inherent resiliency, or the cellulose fibres can be mixed with highly resilient synthetic fibres.

The receiving layer 18 may also include a minor quantity of so-called superabsorbents, i.e. material in the form of fibres, particles, granules, film or the like which is able to absorb and bind body liquid in an amount corresponding to several times the intrinsic weight of the superabsorbents while chemically forming an hydraulic gel.

Seen in a direction from the liquid-permeable casing sheet 1, there is disposed inwardly of the receiving layer 18 a second absorbent layer 19 which is intended to be able to receive and collect relatively large quantities of body liquid in a short period of time. The second absorbent layer, the storage layer 19, is formed from a web of material which has been cut in two longitudinally along a sinusoidal curve 20 which extends along the longitudinally extending centre line 21 of the web, wherein the sinusoidal curve swings or undulates forwards and backwards over the centre line 21. The two web-parts 22, 23 have thereafter been displaced in relation to one another through one half wavelength in the longitudinal direction of the web. This results in the formation of a row of round holes 24 along the web centre line, these holes alternating with intermediate overlapping web-parts 25. The holes 24 constitute a cavity or region of a lower density than the adjacent parts of the web-parts 22,23. One flat surface of the storage layer 19 is arranged in abutment with the receiving layer 18 and the other flat surface is arranged in abutment with a third absorbent layer 26 located inwardly of the storage layer 19 nearest the liquid-impermeable casing sheet 2.

The diaper illustrated in FIG. 1 has its main extension in the XY plane, the X direction being defined by the transverse direction of the diaper and the Y direction being defined by the longitudinal direction of the diaper. The storage layer 19 is comprised advantageously of a material which when wetted with body liquid will expand strongly in the Z direction, i.e. in a direction perpendicular to the XY plane. The manufacture of a particularly suitable material of this kind is described in WO 94/10956. One characteristic feature of this material is that it is produced by dry-forming flash dried cellulose fibres to produce a web having a surface weight of 30–2000 $g/m^2$, which is compressed to a density of between 0.2–1 $g/cm^3$, and that the web is incorporated as an absorbent structure in an absorbent article without subsequent defibration and fluff formation.

Another suitable expanded material is cellulose fluff pulp which has admixed therewith a given quantity of superabsorbent material, preferably at least 10 percent by weight superabsorbent material. The aforedescribed materials are often produced in the form of relatively thin webs, having a thickness of only a few millimeters. The storage layer can therewith be formed from one or more layers of such material.

Other appropriate storage layer materials are compressed foam material or fibre wadding which when wetted will at least partially return to their non-compressed size. When necessary, the materials may be fixated in their compressed states with the aid of some form of water-soluble binder.

If considered suitable, the storage layer 19 may, of course, be produced from a web of material formed conventionally by air-laying cellulose fluff pulp, with or without the admixture of different types of binding fibres or other additives. Different kinds of nonwoven material, tissue layers or other wet-laid fibre structures may also be used. The invention may be applied to all web-like materials used in the manufacture of sanitary absorbent articles.

The third absorbent layer 26, hereinafter referred to as the liquid-dispersion layer 26, is comprised of a material of high density having a high liquid-dispersing and liquid-retaining capacity. As with the storage layer 19, the material described in WO/9410956 is particularly usable in this regard. However, conventional compressed layers of cellulose fluff pulp, absorbent foam material, or different kinds of tissue laminates may be used. The liquid-dispersion layer 26 is generally rectangular in shape and has a smaller extension in the XY plane of the diaper than the receiving layer 18. The liquid-dispersion layer will therefore be surrounded on all sides by a soft, body-friendly material of low liquid dispersion ability. This arrangement affords several advantages. Firstly, no sharp or hard edges on the liquid-dispersion layer 26 are able to come into contact with the wearer's body and chafe or irritate the wearer's skin; and, secondly, any movement of liquid conducted towards the diaper edges in the liquid-dispersion layer 26 is counteracted, therewith considerably reducing the danger of body liquid leaking from the diaper. The edges of the liquid-dispersion layer 26 also form fold indications or directives around which the diaper is able to fold when compressed in the crotch region between the wearer's thighs in use. In this way, the diaper will take a size and shape which is better adapted to the space in the crotch region.

The liquid-dispersion layer 26 is primarily intended to transport body liquid away from that region of the diaper on which the body liquid is first received, i.e. the primary wetting area. The absorbent material in the absorbent body 3 is utilized more effectively in this way. This is achieved by compressing the liquid-dispersion layer 26 relatively heavily, wherewith the layer obtains a high affinity to body liquid and a high liquid dispersion capacity. For the purpose of guiding liquid transportation in the longitudinal direction of the diaper, the liquid-dispersion layer 26 may conveniently be provided with a longitudinally extending compression profile or pattern, in the form of grooves, wave patterns, or like configurations. The liquid-dispersion layer 26 may also include a minor quantity of superabsorbent.

The two storage layer parts 22, 23 are suitably fastened to the liquid-dispersion layer 26, for instance glued thereto, so as to avoid said parts moving within the diaper. Alternatively, the storage layer 19 may be fastened to a separate layer, for instance a layer of tissue or nonwoven, or may be fastened to the receiving layer 18. The storage layer 19 may, of course, be fastened to more than one layer.

As shown in FIG. 2a, the storage layer 19 will have a relatively small thickness prior to the diaper absorbing body liquid. The cavity 24 formed between the two parts of the storage layer 19, however, is sufficient to accommodate the amount of liquid first discharged. The liquid discharged to the diaper will impinge on the liquid-permeable casing sheet 1 thereof within a small limited area, the so-called primary wetting area, and pass quickly down through the casing sheet 1 and the receiving layer 18. The liquid is collected in the holes 24 between the overlapping parts 25 of the storage layer 19, and in the fibre structure proximal to the primary wetting area of the diaper. The liquid is then spread gradually out in the XY plane of the diaper by the absorbent material in the liquid-dispersion layer 26. This absorption process is relatively slow, since it depends on the capillary forces acting between fibres and particles in the absorption material. The fibre structure nearest the wetting area will, in general, not have had time to be emptied of liquid before liquid is again discharged to the diaper.

However, a part of the liquid collected in the holes 24 in the storage layer 19 on the first wetting occasion will be absorbed by the material in said layer. Since this material is preferably of a kind which will expand in the Z direction of the diaper when wetted, the receiving layer 18 and the dispersion liquid layer 23 will move apart in the Z direction, thereby enlarging the cavity 24 between the two absorption layers 18, 26. Consequently, when the diaper is next wetted the space available for instantaneous take-up of liquid will be equally as large or larger than the space that was available on the first wetting occasion. Thus, the rate at which liquid penetrates into the diaper will not decrease to any appreciable extent, but in particularly favourable instances may even increase with repeated wetting of the diaper absorbent body 3.

The parts 25 lying between the holes 24 along the longitudinal centre line 21 of the storage layer 19 are comprised of two layers of overlapping web material. Since the web is relatively thin when dry, the difference in thickness between the different parts of the storage layer 19 are hardly noticeable when the diaper is dry. When wet, however, the overlapping parts 25 swell twice as much as remaining parts of the storage layer 19. This results in the formation of raised or elevated parts 27 along the centre line 21 of the storage layer 19 which further increase the distance between the receiving layer 18 and the liquid-dispersion layer 26 and between the receiving layer 18 and those parts of the storage layer 19 which consist of a single layer of material. This additional cavity 28 serves to make the diaper airy and comfortable to wear in use. The overlapping parts 25 of the storage layer 19 also impart an additional absorption capacity to the diaper along the centre line 21, this additional capacity improving security of the diaper against leakage, particularly in the crotch part 7.

Figure 3:
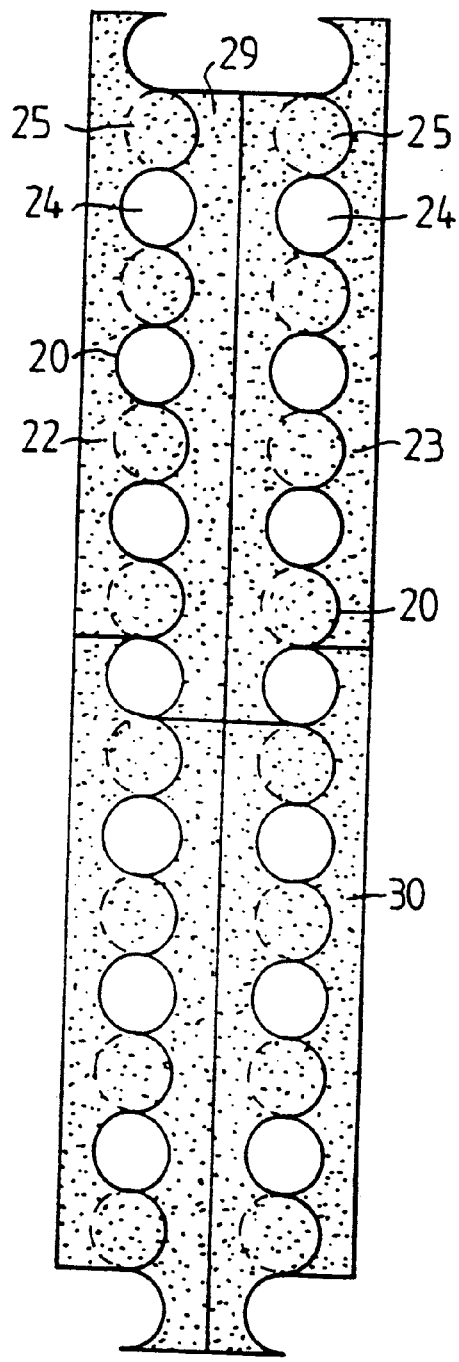
FIGS. 3–7 illustrate different embodiments of webs provided with cavities in accordance with the invention, said webs being shown in a flat state.

FIG. 3 illustrates a web of material in which holes 24 have been formed by first cutting the web 30 along a curved cutting line, and then displacing the thus separated web-parts 22, 23 longitudinally so as to obtain a repeating pattern of openings 24 and overlapping parts 25 in the web 30. The web 30 shown in FIG. 3 has been cut longitudinally along two essentially sinusoidal curves 20. As a result, two longitudinally extending rows of holes 24 with intermediate overlapping parts of material 25 are formed when the edge-parts 22, 23 of the web are displaced in relation to the centre part 29 of the web. Of course, the principle can be applied to produce any desired number of rows of openings in a web. The number of rows of holes is determined in this regard by the number of curved cuts made in the web.

Figure 4:
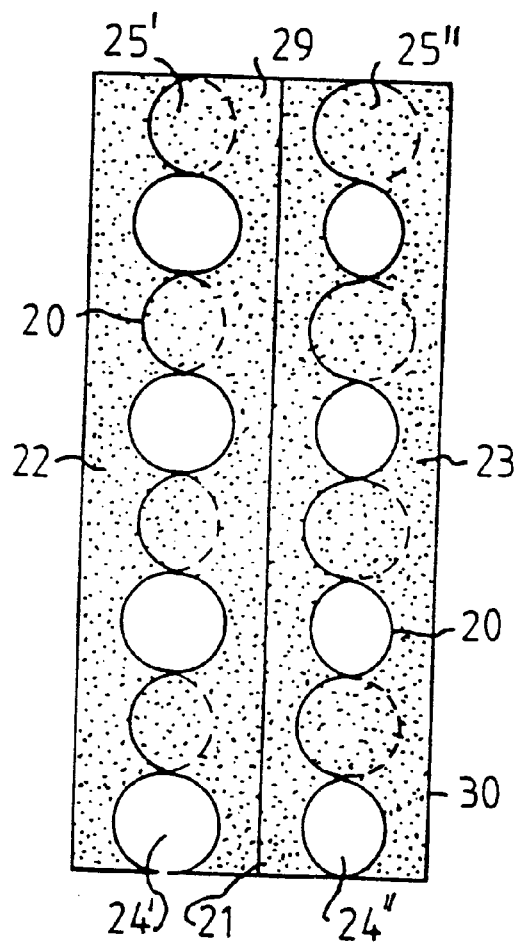

The web 30 shown in FIG. 4 has been cut longitudinally along a sinusoidal dividing curve 20, in the same way as the web 30 shown in FIG. 3. One edge-part 22 of the web 30 has then been displaced both longitudinally and transversely, way from the longitudinal centre line 21 of the web 30. The other edge-part 23 has been displaced both longitudinally and transversely in towards the longitudinal centre line 21 of the web 30. This enables the size of the holes 24', 24" and the size of the overlapping parts 25', 25Δ to be regulated or adjusted. When an edge-part 23 is displaced towards the longitudinal centre line 21 of the web 30, the size of the holes 24" is decreased while obtaining at the same time a larger overlap 25" between the web-parts lying between the holes 24". Correspondingly, the size of the holes 24' is increased, by displacing the edge-part 22 of the web 30 away from the centre line 21.

Figure 5:
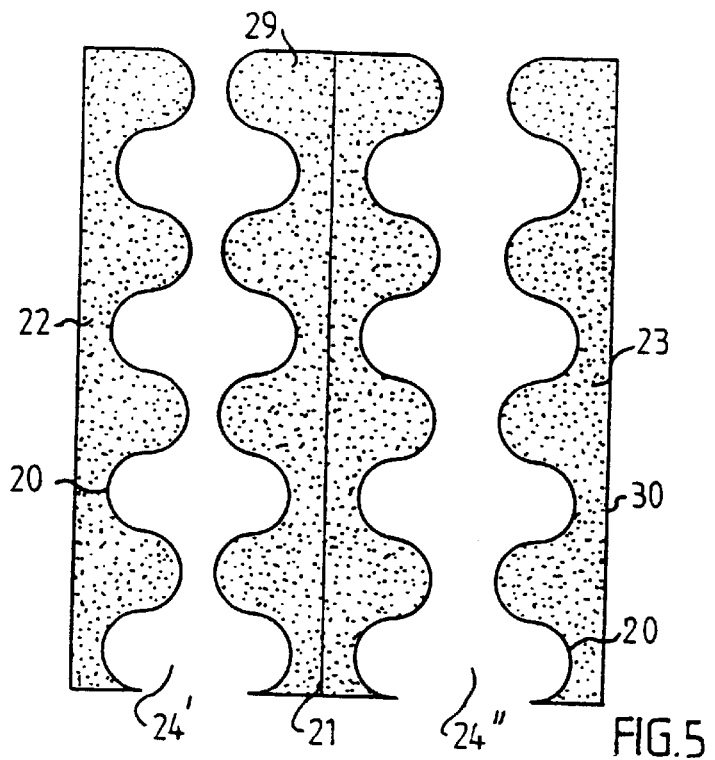

FIG. 5 illustrates how continuous, longitudinally extending openings 24 can be obtained between parts of a web 30 that have been cut along essentially sinusoidal curves 20. The web-parts 22, 23, 29 in FIG. 5 are displaced mutually both in the longitudinal and transversal direction of the web 30, by moving the cut edge-parts 22, 23 laterally in a direction away from the longitudinal centre line 21 of the web 30. The width of the continuous channel-like opening 24', 24" between two web-parts is determined by the distance to which the web-parts are moved apart. FIG. 5 shows two examples of openings 24', 24" of different widths. Naturally, the web 30 may include any desired number of continuous openings of the kind described here.

Figure 6:
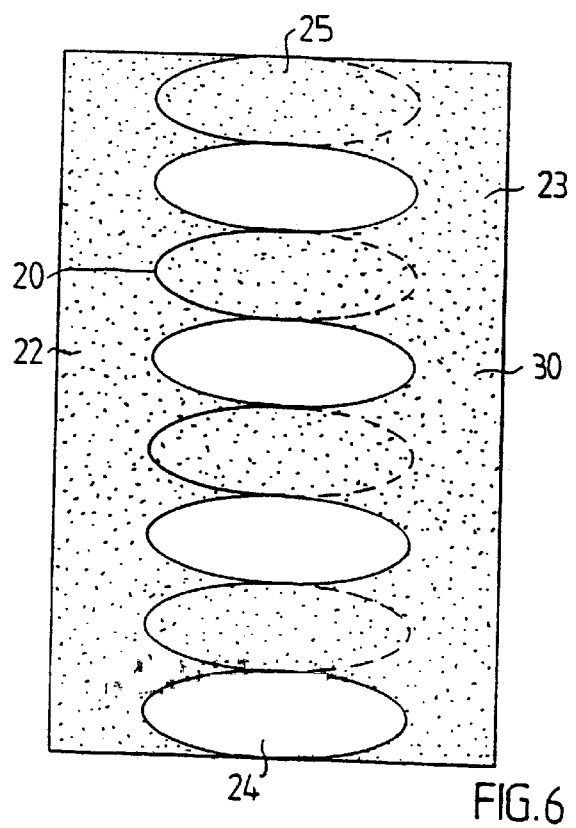

FIG. 6 illustrates a web which has been cut along a sinusoidal curve and displaced through one-half wavelength in its longitudinal direction, so as to form oval holes 24.

Figures 7A, 7B:
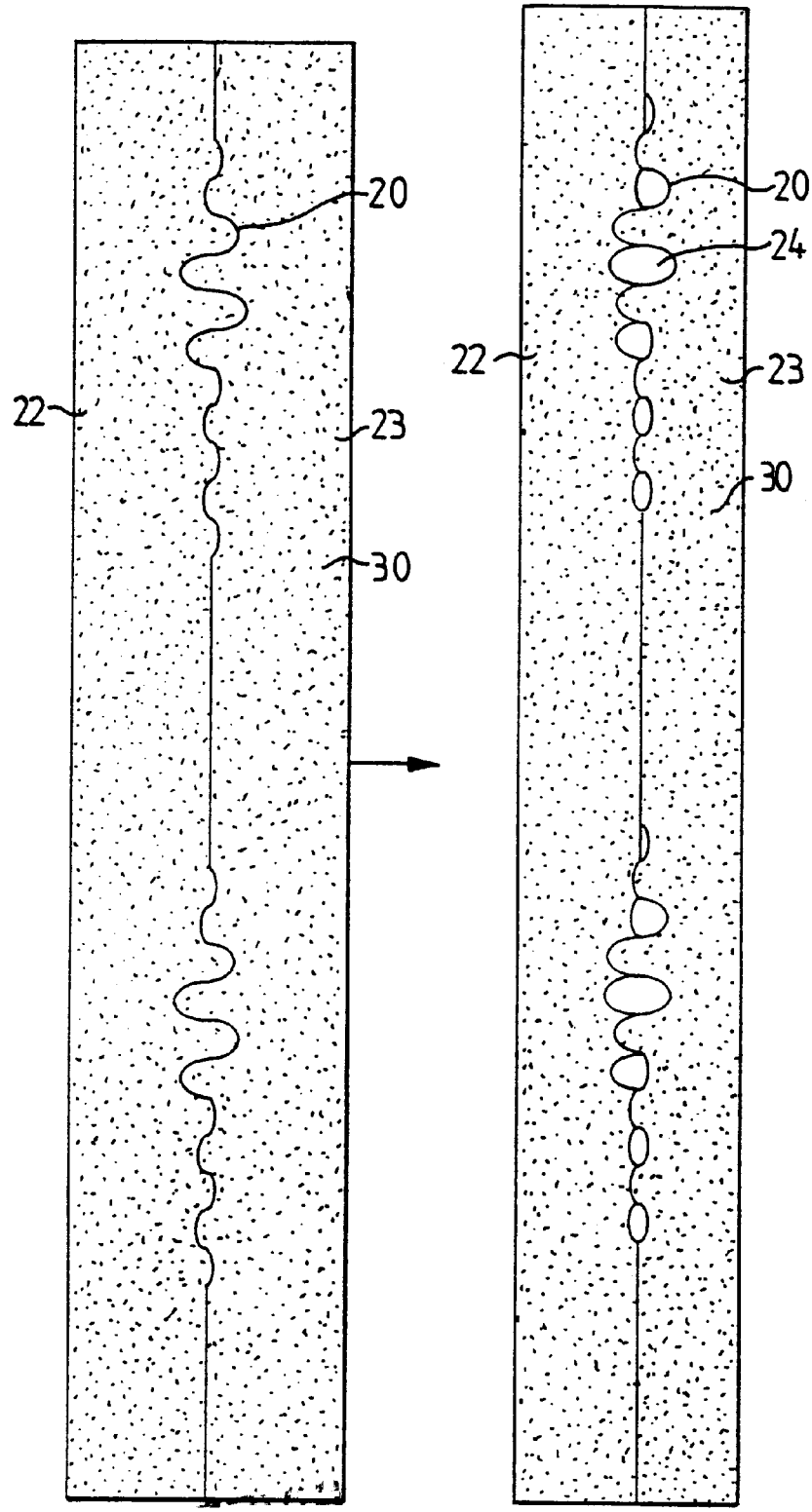

FIGS. 7a and 7b illustrate a web of material 30 which has been cut in a straight line along certain parts of the web and which has been cut along a sinusoidal curve 20 of varying amplitude along other parts of the web. When the web-parts 22, 23 are displaced through one-half wavelength in the longitudinal direction of the web, holes 24 of varying sizes re formed in certain parts of the web 30. The web is clipped or cut appropriately transversely to the straight cut parts and the clipped parts are incorporated in the absorbent body of an absorbent article with the largest hole located in the contemplated wetting area of said article.

The web-parts can be placed in the article with the dividing curves located either in the longitudinal or in the transverse direction of the article. Other curve forms of any desired type can be chosen instead of sinusoidal curves, for instance curves of a sawtooth or square-wave shape. As described above, the amplitude of the waves or undulations may vary. The waves or undulations may also have a varying wavelength, in which case a varying overlap is obtained between the holes when displacing the web-parts to a given extent.

Although the invention has been described in the aforegoing mainly with reference to diapers, it will be understood that the invention can be applied to all types of absorbent articles intended for the absorption of body liquid or fluid. Examples of such articles are diapers and incontinence guards for children and adults, and also sanitary napkins, panty guards, bed protectors, seat protectors, dressings or like articles.

I claim:

1. An absorbent article, comprising:
    a liquid-permeable outer sheet,
    a liquid-permeable outer sheet, and
    an absorbent body which is enclosed between the two outer sheets and which includes a receiving space for receiving and accommodating body liquid or fluid, said space comprising at least one cavity or region of lower density than a density of a part of the absorbent body located adjacent the receiving space generally in the same plane,
    the receiving space is disposed in a storage layer in the absorbent body, wherein the storage layer is formed from a web of material which is divided in a longitudinal direction of the web along a dividing curve which undulates along at least part of its length so as to cross a line extending in the longitudinal direction of the web at least two times to create web-parts; and the web-parts are displaced relative to one another in the plane of the web such that the web-parts will delimit the receiving space therebetween in the plane of the web.

2. An article according to claim 1, wherein the web-parts are displaced relative to one another in the longitudinal direction of the dividing curve such that the web-parts delimit at least one cavity therebetween.

3. An article according to claim 1 wherein the web-parts are displaced in a direction away from one another, in the transverse direction of the web, whereby the storage layer presents a channel-like undulating space which extends between the web-parts.

4. An article according to claim 1, wherein the web-parts are placed in the article with an undulating curve extending either in the longitudinal or in the transversal direction of the article.

5. An article according to claim 1, wherein the dividing curve is generally sinusoidal in shape.

6. An article according to claim 5, wherein the web-parts are displaced mutually in the longitudinal direction of the dividing curve such that the maxima of the dividing curve on both sides of the longitudinal line in the web will be located generally opposite one another, and so that a line extending generally perpendicular to the longitudinal line through the web can be drawn through the maxima of said dividing curve, whereby the web-parts define therebetween a row of generally circular or oval holes alternating with overlapping web-parts in the longitudinal direction of the web.

7. An article according to claim 1, wherein the undulations of the undulating curve vary in amplitude such that the receiving spaces defined between the web parts will have varying sizes.

8. An article according to claim 1, wherein portions of the web-parts that lie adjacent the receiving space include a material which when wetted will increase in volume in a direction generally perpendicular to a surface of the article, whereby the size of the receiving space will also increase perpendicular to the surface as a result of wetting of the article.

9. An article according to claim 1, wherein the liquid accommodating receiving space is comprised of one or more holes which extend through the thickness of the storage layer.

10. An article according to claim 1, wherein the receiving space is comprised of at least one channel-like cavity extending in the longitudinal direction of the article.

11. An article according to claim 1, wherein the storage layer is formed from particle material which includes flash-dried cellulose fibres which have been dry-formed to provide a web having a surface weight of 30–2000 g/m$^2$ and compressed to a density between 0.2–1.2 g/cm$^3$; and in that the web has been incorporated in the article without subsequent defibration and fluff formation.

12. An article according to claim 1, wherein the storage layer is formed from an air-laid web of cellulose fibres which has been compressed to a dry-formed sheet having a first density of between 0.2–1.2 g/cm$^3$, whereafter the sheet has been softened mechanically to a second density lower than the original density and therewith delaminated, so as to form a plurality of incompletely separated thin fibre layers which have a density corresponding to the first density.

13. An article according to claim 1, wherein the storage layer is formed from an air-laid web of cellulose fibres which has been compressed to a density of at least 0.1 g/cm$^3$, preferably at least 0.12 g/cm3.

14. An article according to claim 1, wherein the storage layer is formed from an air-laid web of cellulose fibres in which there is admixed a given proportion of thermoplastic fibres and the fibre web has been thermobonded.

15. An article according to claim 13, wherein the storage layer also includes a given proportion of superabsorbent material.

16. An article according to claim 1, wherein the storage layer is formed from a web of material having a first thickness and including resilient material, said web having been compressed perpendicular to a plane through the web to a second thickness and bound in its compressed state with a binder which will dissolve in body liquid or fluid, wherein bonding of the web ceases when the web is wetted and the web returns at least partially to its first thickness.

17. An article according to claim 16, wherein the storage layer is formed from a compressed foam material which expands in its thickness direction when wetted.

18. An article according to claim 16, wherein the storage layer is formed from a compressed fibre web which is comprised at least partially of fibres that have a given resiliency in a wet state.

19. An article according to claim 1 wherein the storage layer volume taken up by the receiving space is greatest within an area of the article which is intended to be wetted first by body liquid.

20. An article according to claim 19, wherein the proportion of storage layer forming the receiving space decreases in a direction away from said area of the article.

21. An article according to claim 1, wherein the web forming the storage layer is divided along more than one dividing curve extending in the longitudinal direction of the web.

* * * * *

UNITED STATES PATENT AND TRADEMARK OFFICE
CERTIFICATE OF CORRECTION

PATENT NO.    : 5,961,507
DATED         : October 15, 1999
INVENTOR(S)   : Urban Widlund It is certified that error appears in the above-identified patent and that said Letters Patent is hereby corrected as shown below:

Column 10,
Line 37, delete "a liquid-permeable outer sheet, and" and insert -- a liquid-impermeable outer sheet, and --, therefor.

Signed and Sealed this

Thirteenth Day of May, 2003

JAMES E. ROGAN
*Director of the United States Patent and Trademark Office*